(12) United States Patent
Ekwuribe et al.

(10) Patent No.: US 6,479,692 B1
(45) Date of Patent: Nov. 12, 2002

(54) METHODS OF SYNTHESIZING ACYLANILIDES INCLUDING BICALUTAMIDE AND DERIVATIVES THEREOF

(75) Inventors: Nnochiri N. Ekwuribe, Cary, NC (US); Kenneth D. James, Jr., Mebane, NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 09/847,229

(22) Filed: May 2, 2001

(51) Int. Cl.$^7$ ............................................. C07C 255/50
(52) U.S. Cl. ...................................................... 558/413
(58) Field of Search ........................................ 558/413

(56) References Cited

U.S. PATENT DOCUMENTS

| | | | |
|---|---|---|---|
| 4,420,639 A | 12/1983 | Lake et al. ................... | 568/328 |
| 4,472,382 A | 9/1984 | Labrie et al. ................ | 424/177 |
| 4,636,505 A | 1/1987 | Tucker ........................ | 514/256 |
| 5,389,613 A | 2/1995 | Labrie et al. ................. | 514/15 |
| 5,777,134 A | 7/1998 | Bakshi et al. ................ | 549/276 |
| 5,985,868 A | 11/1999 | Gray .......................... | 514/220 |
| 5,994,362 A | 11/1999 | Gormley et al. ............. | 514/284 |
| 6,019,957 A | * 2/2000 | Miller et al. ................. | 514/220 |
| 6,071,957 A | * 6/2000 | Miller et al. ................. | 514/522 |

FOREIGN PATENT DOCUMENTS

| | | | |
|---|---|---|---|
| WO | WO94/08986 | 4/1994 | ......... C07D/311/22 |
| WO | WO95/19770 | 7/1995 | ......... A61K/31/275 |
| WO | WO98/55153 | 12/1998 | .......... A61K/49/04 |

OTHER PUBLICATIONS

Wright et al. Journal of Medicinal Chemistry, 1978, vol. 21, No. 9, pp 930–934.*

Marx et al. J. Med. Chem. 1988, 31, 858–863.*

Tucker et al., "Resolution of the Nonsteroidal Antiandrogen 4'-Cyano-3-[(4-fluorophenyl) sulfonyl]-2-hydroxy-2-methyl-3'-(trifluoromethyl)-propionanilide and the Determination of the Absolute Configuration of the Active Enantiomer", *J. Med. Chem.*, 31(4) 885–887 (1988).

International Search Report corresponding to International Application No. PCT/US00/41609; mailed Apr. 12, 2001.

Tucker et al., "Nonsteroidal Antiandrogens. Synthesis and Structure–Activity Relationships of 3–Substituted Derivatives of 2–Hydroxypropionanilides," *J. Med. Chem.*, 31(5) 954–959 (1988).

Casodex (bicalutamide, 50 mg tablets) Professional Information Brochure, <http://www.astrazeneca–us.com/pi/pib_casodex.htm>, pp. 1–9, Jun. 26, 2000.

Fournier et al., "(Hydroxy-2 Alkyl)-et(Hydroxy-3 Alkyl)-Phénylsulfones à Activité Hypolipidémiante," *Eur. J. Med. Chem.*, 17(1) 53–58 (1982) (French with English Abstract).

* cited by examiner

*Primary Examiner*—Joseph K. McKane
*Assistant Examiner*—Kamal Saeed
(74) *Attorney, Agent, or Firm*—Myers Bigel Sibley & Sajovec, P.A.

(57) ABSTRACT

Methods of synthesizing an acylanilide

Formula V

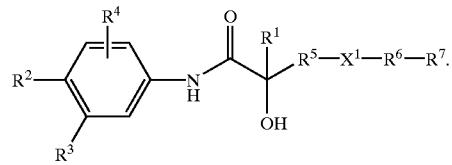

46 Claims, No Drawings

METHODS OF SYNTHESIZING ACYLANILIDES INCLUDING BICALUTAMIDE AND DERIVATIVES THEREOF

FIELD OF THE INVENTION

The present invention relates to methods of synthesizing organic compounds, and more particularly to methods of synthesizing pharmaceutical compounds and their derivatives.

BACKGROUND OF THE INVENTION

Androgen deprivation is a common treatment for persons with prostate cancer. Various non-steroidal antiandrogens are known for use in the treatment of prostate cancer. For example, bicalutamide is often used in the treatment of prostate cancer. Bicalutamide is commercially available as Casodex® (bicalutamide) from AstraZeneca Pharmaceuticals.

The chemical name of bicalutamide is N-[4-cyano-3-(trifluoromethyl)phenyl]-3-[(4-fluorophenyl)sulfonyl]-2-hydroxy-2-methyl-propanamide (+−). The structural formula of bicalutamide is:

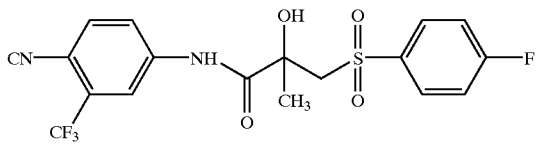

The β-carbon atom in the propanamide is a chiral carbon. As a result, bicalutamide is an optically active compound.

Such optically active compounds exist as a pair of stereoisomers that are identical with the notable exception that they are non-superimposable mirror images of one another. A specific stereoisomer, such as the R isomer, may be referred to as an enantiomer. A mixture of R and S enantiomers may be referred to as a racemic mixture.

U.S. Pat. No. 4,636,505 to Tucker proposes various methods of synthesizing racemic mixtures of bicalutamide and/or its derivatives.

In Tucker et al., Nonsteroidal Antiandrogens. Synthesis and Structure-Activity Relationships of 3-Substituted Derivatives of 2-Hydroxypropionanilides, 31 J. MED. CHEM. 954–959 (1988), the authors propose two general synthetic routes, Scheme I and Scheme II, that may be used to prepare acylanilides.

U.S. Pat. No. 5,985,868 to Gray proposes synthesizing racemic mixtures of bicalutamide using methods as described in U.S. Pat. No. 4,636,505 to Tucker, and obtaining the (−) isomer of bicalutamide by resolution of the enantiomers of bicalutamide or of intermediates thereto using fractional crystallization or chromatography of diastereomeric esters of chiral acids. Gray notes that other standard methods of resolution such as simple crystallization and chromatographic resolution can also be used.

In Howard Tucker et al., Resolution of the Nonsteroidal Antiandrogen 4'-Cyano-3-[(4-fluorophenyl)sulfonyl]-2-hydroxy-2-methyl-3'-(trifluoromethyl)-propioanilide and the Determination of the Absolute Configuration of the Active Enantiomer, 31 J. MED. CHEM. 885–887 (1988), the authors propose an asymmetric synthesis of(S)-bicalutamide using the N-methacrylamide of (S)-proline as a starting material. The authors state that this approach is not suitable for the general synthesis of the active enantiomers of analogous anti-androgens, which would require the inaccessible and expensive (R)-proline as a starting material.

U.S. Pat. No. 6,019,957 to Miller et al. proposes an asymmetric synthesis of (R)-bicalutamide using (R)-proline as a starting material.

It would be desirable to provide more effective methods for synthesizing bicalutamide and/or its derivatives and/or intermediates.

SUMMARY OF THE INVENTION

Embodiments of the present invention provide improved methods for synthesizing acylanilides, particularly bicalutamide and/or its functional derivatives. Methods according to embodiments of the present invention may provide a racemic mixture of bicalutamide using commercially available reagents in fewer steps than the conventional methods described above, which may reduce the overall synthesis time by more than 50 percent compared to these methods. Methods according to embodiments of the present invention may result in yields greater than 50 percent, 60 percent, 70 percent or more. Moreover, methods according to embodiments of the present invention may be performed at or near room temperature. These reaction conditions may provide an energy savings when compared to the conventional methods described above, which involve, for example, refluxing conditions and cooling to 5° C.

According to embodiments of the present invention, methods of synthesizing an acylanilide such as bicalutamide or its functional derivatives are provided. The methods include contacting a compound having the structure of Formula I:

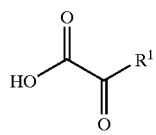

Formula I wherein
$R^1$ is substituted or unsubstituted alkyl or haloalkyl; with a compound having the structure of Formula II:

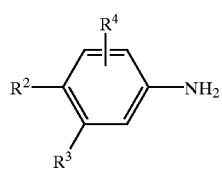

Formula II wherein
$R^2$ is cyano, carbamoyl, nitro, fluoro, chloro, bromo, iodo, or hydrogen; or alkyl, alkoxy, alkanoyl, alkylthio, alkylsulfinyl, alkylsulfonyl, perfluoroalkyl, perfluoroalkylthio, perfluoroalkylsulfinyl, or perfluoroalkylsulfonyl each being substituted or unsubstituted and having up to 4 carbon atoms; or phenyl, phenylthio, phenylsulfinyl or phenylsulfonyl each being susbstituted or unsubstituted;
$R^3$ is cyano, carbamoyl, nitro, fluoro, chloro, bromo or iodo; or alkyl, alkoxy, alkanoyl, alkylthio, alkylsulfinyl, alkylsulfonyl, perfluoroalkyl, perfluoroalkylthio, perfluoroalkylsulfinyl or perfluoroalkylsulfonyl each being substituted or unsubstituted and having up to 4 carbon atoms; or phenyl, phenylthio, phenylsulfinyl or phenylsulfonyl each being substituted or unsubstituted; and R⁴ is hydrogen or halogen;

under conditions sufficient to provide a compound having the structure of Formula III:

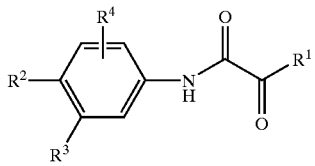

Formula III and treating the compound of Formula III under conditions sufficient to provide an acylanilide. The compound of Formula I is most preferably pyruvic acid.

In embodiments of the present invention, the compound of Formula III is addition reacted with a compound having the structure of Formula IV:

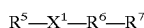

Formula IV wherein

R⁵ is substituted or unsubstituted alkyl having up to 6 carbon atoms;

R⁶ is a direct link, or substituted or unsubstituted alkyl having up to 6 carbon atoms;

R⁷ is alkyl, alkenyl, hydroxyalkyl or cycloalkyl each being substituted or unsubstituted and having up to 6 carbons; or R⁷ is phenyl which bears one, two or three substituents independently selected from hydrogen, halogen, nitro, carboxy, carbamoyl and cyano, and alkyl, alkoxy, alkanoyl, alkylthio, alkylsulfinyl, alkylsulfonyl, perfluoroalkyl, perfluoroalkoxy, perfluoroalkylthio, perfluoroalkylsulfinyl, perfluoroalkylsulfonyl, alkoxycarbonyl and N-alkylcarbamoyl each of up to 4 carbon atoms, and phenyl, phenylthio, phenylsulfinyl and phenylsulfonyl; or R⁷ is naphthyl; or R⁷ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulfinyl or alkylsulfonyl each of up to 4 carbon atoms, or oxy or hydroxy substituents, or which if sufficiently saturated may bear one or two oxo substituents; and X¹ is oxygen, sulfur, sulfinyl (—SO—), sulfonyl (—SO₂—), imino (—NH—) or alkylimino (—NR⁸—) where R⁸ is alkyl having up to 6 carbon atoms;

under conditions sufficient to provide an acylanilide having the structure of Formula V:

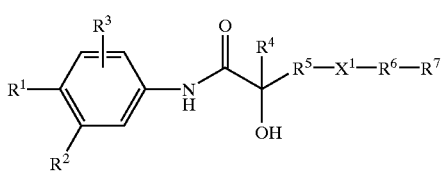

Formula V

The acylanilide is most preferably bicalutamide or a functional derivative thereof. While methods according to embodiments of the present invention generally yield acylanilide compositions having both R and S enantiomers in substantially equal quantities, embodiments of the present invention resolve these acylanilide compositions (e.g., bicalutamide products) to provide compositions comprising more than about 60 percent R enantiomer.

Methods according to embodiments of the present invention provide a more efficient synthesis route for acylanilides, particularly bicalutamide and/or its functional derivatives. Methods of the present invention may reduce the number of steps as well as the overall synthesis time compared to conventional methods of synthesizing bicalutamide. Moreover, methods of the present invention may provide an overall yield that is greater than 50 percent and preferably even greater than 70 percent, which is higher than the overall yield provided by conventional methods of synthesizing bicalutamide. Furthermore, as methods of the present invention may be performed at or near room temperature, these methods may provide an energy savings when compared to conventional methods of synthesizing bicalutamide.

DETAILED DESCRIPTION OF PREFERRED EMBODIMENTS

The invention will now be described with respect to preferred embodiments described herein. It should be appreciated however that these embodiments are for the purpose of illustrating the invention, and are not to be construed as limiting the scope of the invention as defined by the claims.

As used herein, the term "functional derivative" is used to describe a derivative of a parent compound that has the same or substantially similar pharmacological activity as the parent compound.

As used herein, the term "between" should be interpreted to include the end-points. The term "up to" should be interpreted to include the upper limit.

Methods of synthesizing an acylanilide according to embodiments of the present invention include contacting a compound having the structure of Formula I:

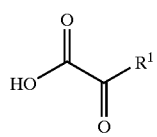

Formula I with a compound having the structure of Formula II:

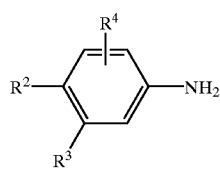

Formula II under conditions sufficient to provide a compound having the structure of Formula III:

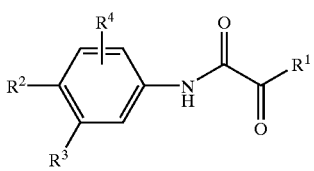

Formula III and treating the compound of Formula III under conditions sufficient to provide an acylanilide, wherein the substituents $R^1$–$R^4$ are as described below.

$R^1$ is substituted or unsubstituted alkyl or haloalkyl. $R^1$ is preferably substituted or unsubstituted alkyl having up to 4 carbon atoms. $R^1$ is preferably substituted or unsubstituted alkyl having 1 or 2 carbon atoms. $R^1$ is more preferably unsubstituted alkyl having 1 or 2 carbon atoms, and is most preferably methyl.

$R^2$ is cyano, carbamoyl, nitro, fluoro, chloro, bromo, iodo, or hydrogen; or alkyl, alkoxy, alkanoyl, alkylthio, alkylsulfinyl, alkylsulfonyl, perfluoroalkyl, perfluoroalkylthio, perfluoroalkylsulfinyl, or perfluoroalkylsulfonyl each being substituted or unsubstituted and having up to 4 carbon atoms (e.g., methylthio, ethylthio, methylsulfinyl, methylsulfonyl, trifluoromethyl, pentafluoromethyl, trifluoromethylthio, trifluoromethylsulfinyl or trifluoromethylsulfonyl); or phenyl, phenylthio, phenylsulfinyl or phenylsulfonyl each being susbstituted or unsubstituted. $R^2$ is preferably selected from the group consisting of cyano, nitro, chloro, perfluoroalkyl, perfluoroalkoxy, perfluoroalkylthio, perfluoroalkylsulfinyl and perfluoroalkylsulfonyl. $R^2$ is most preferably cyano.

$R^3$ is cyano, carbamoyl, nitro, fluoro, chloro, bromo or iodo; or alkanoyl, alkylthio, alkylsulfinyl, alkylsulfonyl, perfluoroalkyl, perfluoroalkylthio, perfluoroalkylsulfinyl or perfluoroalkylsulfonyl each being substituted or unsubstituted and having up to 4 carbon atoms (e.g., methylthio, ethylthio, methylsulfinyl, methylsulfonyl, trifluoromethyl, pentafluoromethyl, trifluoromethylthio, trifluoromethylsulfinyl or trifluoromethylsulfonyl); or phenyl, phenylthio, phenylsulfinyl or phenylsulfonyl each being substituted or unsubstituted. $R^3$ is preferably selected from the group consisting of perfluoroalkyl, perfluoroalkoxy, perfluoroalkylthio, perfluoroalkylsulfinyl and perfluoroalkylsulfonyl each having up to 4 carbon atoms. $R^3$ is more preferably perfluoroalkyl having 1 or 2 carbon atoms. $R^3$ is most preferably trifluoromethyl.

$R^4$ is hydrogen or halogen. When $R^4$ is halogen, $R^4$ is preferably fluoro, chloro, bromo or iodo. $R^4$ is preferably hydrogen.

In a preferred embodiment, the compound of Formula I is contacted with the compound of Formula II in the presence of a carboxylic acid halogenating compound. The carboxylic acid halogenating compound may be various compounds as will be understood by those skilled in the art including, but not limited to, thionyl halides (e.g., thionyl chloride and thionyl bromide), phosphorus trihalides (e.g., phosphorus tribromide and phosphorus triiodide), phosphorus pentahalides, oxalyl halides, or phosgene. The carboxylic acid halogenating compound is preferably thionyl chloride or thionyl bromide. The ratio on a molar basis of the carboxylic acid halogenating compound to the compound of Formula I is preferably between about 1:3 and about 3:1, more preferably between about 1:2 and about 2:1, and most preferably about 1:1. The compound of Formula I is preferably activated by (reacts with) the carboxylic acid halogenating compound to provide an acyl halide. While the acyl halide is preferably formed in situ (i.e., in the presence of the compound of Formula II), it is to be understood that the compound of Formula I may be activated by the carboxylic acid halogenating compound to provide the acyl halide in a first step, followed by the step of contacting the acyl halide with the compound of Formula II.

In a preferred embodiment, the acyl halide reacts with the compound of Formula II to provide the compound of Formula III. The ratio on a molar basis of the compound of Formula II to acyl halide is preferably between about 1:4 and about 1:12. More preferably, the ratio is between about 1:6 and about 1:10. Most preferably, the ratio is between about 1:7 and about 1:9. Applicants have unexpectedly found that using these preferred ratios of the compound of Formula II to acyl halide may result in yields of the compound of Formula III that are greater than about 70 percent.

The step of contacting the compound of Formula I with the compound of Formula II may be carried out at various temperatures, as will be understood by those skilled in the art. This step is preferably carried out at a temperature between about −5° C. and about 40° C., is more preferably carried out at a temperature between about 20° C. and about 30° C., and is most preferably carried out at about room temperature. Performing this step within the preferred ranges may result in a yield of the compound of Formula III that is greater than 70 percent. Additionally, these preferred temperatures may result in synthesis methods that require less energy than conventional methods, resulting in reduced costs.

The step of contacting the compound of Formula I with the compound of Formula II may be carried out in the presence of various solvents, as will be understood by those skilled in the art. Preferably, the solvent is an aprotic solvent such as, for example, N,N-dimethylacetamide (DMA), N,N-dimethylformamide (DMF), dimethyl sulfoxide, hexaniethylphosphoric triamide, tetrahydrofuran (THF), dioxane, diethyl ether, methyl t-butyl ether (MTBE), toluene, benzene, hexane, pentane, N-methylpyrollidinone, tetrahydronaphthalene, decahydronaphthalene, dimethoxyethane, methylene chloride, chloroform, 1,2-dichlorobenzene, 1,3-dimethyl-2-imidazolidinone, or a mixture thereof. More preferably, the solvent is DMA or DMF, and most preferably the solvent is DMA.

According to embodiments of the present invention, yields of the compound of Formula III are preferably greater than about 70 percent, more preferably greater than about 75 percent, and most preferably greater than about 80 percent.

The compound of Formula III may be treated under various conditions to provide an acylanilide according to the present invention. In a preferred embodiment, the compound of Formula III is contacted with a compound having the structure of Formula IV:

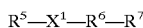  Formula IV under conditions sufficient to provide an acylanilide. Preferably, the compound of Formula III is addition reacted with the compound of Formula IV under conditions sufficient to provide the acylanilide. The acylanilide preferably has a hydroxyl moiety at its β position (i.e., at a carbon atom adjacent to the carbonyl group). More preferably, the acylanilide has the structure of Formula V:

Formula V

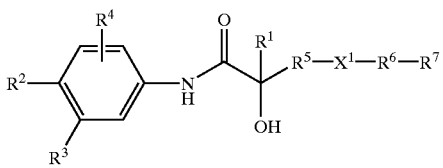

wherein the substituents $R^1$–$R^4$ are as described above, and wherein the substituents $R^5$–$R^7$ and $X^1$ are described as follows.

$R^5$ is substituted or unsubstituted alkyl (alkylene) having up to 6 carbon atoms. $R^5$ preferably is an unsubstituted alkyl (alkylene) having 1, 2 or 3 carbon atoms. $R^5$ is more preferably an unsubstituted alkyl (alkylene) having 1 or 2 carbon atoms. Most preferably, $R^5$ is methyl (methylene).

$R^6$ is a direct link, or substituted or unsubstituted alkylene having up to 6 carbon atoms. Preferably, $R^6$ is a direct link or an unsubstituted alkylene having 1, 2 or 3 carbon atoms. More preferably, $R^6$ is a direct link or an unsubstituted alkylene having 1 or 2 carbon atoms. Most preferably, $R^6$ is a direct link.

$R^7$ is alkyl, alkenyl, hydroxyalkyl or cycloalkyl each being substituted or unsubstituted and having up to 6 carbons (e.g., methyl, ethyl, n-propyl, isopropyl, n-butyl, allyl, 2-methylprop-2-enyl, 2-hydroxyethyl, cyclopentyl or cyclohexyl); or $R^7$ is phenyl which bears one, two or three substituents independently selected from hydrogen, halogen, nitro, carboxy, carbamoyl and cyano, and alkyl, alkoxy, alkanoyl, alkylthio, alkylsulfinyl, alkylsulfonyl, perfluoroalkyl, perfluoroalkoxy, perfluoroalkylthio, perfluoroalkylsulfinyl, perfluoroalkylsulfonyl, alkoxycarbonyl and N-alkylcarbamoyl each of up to 4 carbon atoms and phenyl, phenylthio, phenylsulfinyl and phenylsulfonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulfinyl or alkylsulfonyl each of up to 4 carbon atoms, or oxy or hydroxy substituents, or which if sufficiently saturated may bear one or two oxo substituents (e.g., furyl, thienyl, pyrrolyl, pyridyl, imidazolyl, thiazolyl, pyrimidinyl, thiadiazolyl, triazolyl, benzimidazolyl, benzothiazolyl, indolyl, benzothienyl, benzofuryl, quinolyl, isoquinolyl or 1,2-dihydro-2-oxoquinolyl). $R^7$ is preferably phenyl which bears one, two or three substituents independently selected from hydrogen and halogen. More preferably, $R^7$ is halophenyl. Most preferably, $R^7$ is 4-fluorophenyl.

$X^1$ is oxygen, sulfur, sulfinyl (—SO—), sulfonyl (—$SO_2$—), imino (—NH—) or alkylimino (—$NR^8$—) where $R^8$ is alkyl having up to 6 carbon atoms. $X^1$ is preferably sulfur, sulfinyl (—SO—), sulfonyl (—$SO_2$—), imino (—NH—). $X^1$ is more preferably sulfur, sulfinyl (—SO—), or sulfonyl (—$SO_2$—).

In a preferred embodiment, the compound of Formula IV is addition reacted with the compound of Formula III to provide the acylanilide of Formula V by contacting the compound of Formula IV with an organometallic compound to provide an intermediate compound, and contacting the intermediate compound with the compound of Formula III to provide the acylanilide of Formula V. The organometallic compound, which is capable of deprotonating the compound of Formula IV, may be various organometallic compounds as will be understood by those skilled in the art including, but not limited to, Grignard reagents, alkyllithium, lithium diisopropylamide, lithium hexamethyl disilazide, or a mixture thereof. The organometallic compound is preferably alkyllithium and is more preferably butyllithium. The intermediate compound is preferably contacted with the compound of Formula III by slowly adding the compound of Formula III (e.g., dropwise) to a solution containing the intermediate compound. The ratio on a molar basis of the compound of Formula III to intermediate compound is preferably between about 1:2 and about 1:10, and is more preferably between about 1:2 and about 1:5. Controlling the rate at which the compound of Formula III is added to within the preferred ranges and/or ensuring that the ratio of the compound of Formula III to intermediate compound is within the preferred ranges may result in yields of the acylanilide that are higher than those obtained using conventional synthesis methods.

The step of contacting the compound of Formula III with the compound of Formula IV may be carried out at various temperatures, as will be understood by those skilled in the art. However, this step is preferably carried out at a temperature between about −5° C. and about 40° C., is more preferably carried out at a temperature between about 20° C. and about 30° C., and is most preferably carried out at about room temperature. Applicants have unexpectedly found that this reaction may be carried out at these preferred temperatures while still obtaining a yield of acylanilide that is greater than about 85 percent. These preferred temperatures may require less energy than conventional methods, resulting in reduced costs.

The step of contacting the compound of Formula III with the compound of Formula IV may be carried out in the presence of various solvents, as will be understood by those skilled in the art. Preferably, the solvent is an aprotic solvent such as, for example, tetrahydrofuran (THF), dioxane, ether, dimethoxyethane, dichloromethane, benzene or a mixture thereof. More preferably, the solvent is THF, dioxane or ether, and most preferably the solvent is THF.

According to embodiments of the present invention, yields of the acylanilide derived from the compound of Formula III are preferably greater than 80 percent, more preferably greater than about 85 percent, and most preferably greater than about 90 percent.

According to embodiments of the present invention, the overall yield of the acylanilide is preferably greater than 50 percent, is more preferably greater than 60 percent and is most preferably greater than 70 percent. As used herein, the overall yield is the yield that is calculated by multiplying the yield of each individual step in the synthetic procedure.

Preferred acylanilides that may be synthesized according to embodiments of methods of the present invention have the structure of Formula V above wherein $R^1$ is methyl or trifluoromethyl, $R^2$ is cyano, nitro, trifluoromethyl, chloro, methyl or methoxy, $R^3$ is cyano, nitro, trifluoromethyl or chloro, $R^4$ is hydrogen, $R^5$ is methylene, ethylene or ethylidene, $R^6$ is a direct link or methylene, $R^7$ is alkyl, alkenyl, hydroxyalkyl or cycloalkyl each having up to 6 carbon atoms, or phenyl which is unsubstituted or which bears one fluoro, chloro, cyano, nitro, methoxy or methylthio substituent, or thienyl, imidazolyl, thiazolyl, benzothiazolyl, thiadiazolyl, pyridyl or pyrimidinyl which is unsubstituted or which bears one chloro, bromo or methyl substituent, and $X^1$ is oxygen, sulfur, sulfinyl, sulfonyl, imino or methylimino.

Particularly preferred acylanilides that may be synthesized according to embodiments of methods of the present invention have the structure of Formula V above wherein $R^1$ is methyl, $R^2$ is cyano or nitro, $R^3$ is trifluoromethyl, $R^4$ is hydrogen, $R^5$ is methylene, $R^6$ a direct link, $R^7$ is alkyl having up to 3 carbon atoms, preferably ethyl, or is allyl, phenyl, p-fluorphenyl, thiazol-2-yl, 4-methylthiazol-2-yl, 5-methyl-1,3,4-thiadiazol-2-yl or 2-pyridyl, and $X^1$ is sulfur, sulfonyl or sulfinyl.

The following acylanilides are preferably synthesized according to embodiments of methods of the present invention: 3-chloro-4-cyano-N-((2-hydroxy-2-methyl-3-ethylthio)propionyl)aniline; 3-chloro-4-cyano-N-((2-hydroxy-2-methyl-3-ethylsulfonyl)propionyl)aniline; 3-trifluoromethyl-4-cyano-N-((2-hydroxy-2-methyl-3-phenylsulfonyl)propionyl)aniline; 3-trifluoromethyl-4-cyano-N-((2-hydroxy-2-methyl-3-ethylsulfonyl)propionyl)aniline; 3-trifluoromethyl-4-cyano-N-((2-hydroxy-2-methyl-3-phenylsulfonyl)propionyl)aniline; 3-trifluoromethyl-4-nitro-N-((2-hydroxy-2-methyl-3-ethylsulfonyl)propionyl)aniline; 3-chloro-4-nitro-N-((2-hydroxy-2-methyl-3-phenylthio)propionyl)aniline; 3-trifluoromethyl-4-nitro-N-((2-hydroxy-2-methyl-3-(thiazol-2yl)thio)propionyl)aniline; 3-tri fluoromethyl-4-nitro-N-((2-hydroxy-2-methyl-3-allylthio)propionyl)aniline; 3-trifluoromethyl-4-nitro-N-((2-hydroxy-2-methyl-3-(p-fluorophenyl)thio)propionyl)aniline; 3-trifluoromethyl-4-nitro-N-((2-hydroxy -2-methyl-3-(pyrid-2ylthio)propionyl)aniline; 3-trifluoromethyl-4-nitro-N-((2-hydroxy-2-methyl-3-(5-methyl-1,3,4-thiadiazol-2-ylthio)propiony 3-trifluoromethyl-4-nitro-N-((2-hydroxy-2-methyl-3-(4-methylthiazol-2-ylthio)propionyl)aniline; 3-trifluoromethyl-4-nitro-N-((2-hydroxy-2-methyl-3-(pyrid-2-ynsulfonyl)propionyl)aniline; 3-trifluoromethyl-4-nitro-N-((2-hydroxy-2-methyl-3-(p-fluorophenylsulfonyl)propionyl)aniline; 3-trifluoromethyl-4-cyano-N-((2-hydroxy-2-methyl-3-(thiazol-2-ylthio)propionyl)aniline; 3-trifluoromethyl-4-cyano-N-((2-hydroxy-2-methyl-3-(pyrid-2-ylthio)propionyl)aniline; 3-trifluoromethyl-4-cyano-N-((2-hydroxy-2-methyl-3-methylthiopropionyl)aniline; 3-trifluoromethyl-4-cyano-N-((2-hydroxy-2-methyl-3-(p-fluorophenylthio)propionyl)aniline; 3-trifluoromethyl-4-cyano-N-((2-hydroxy-2-methyl-3-(p-fluorophenylsulfonyl)propionyl)aniline.

In a particularly preferred embodiment, bicalutamide is synthesized according to methods of the present invention. The reaction conditions (e.g., temperature, compound ratios, solvents, etc.) are as described above and will not be further described. According to this particularly preferred embodiment, a compound having the structure of Formula VI:

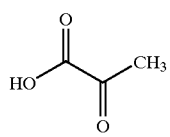

Formula VI is contacted with a compound having the structure of Formula VII:

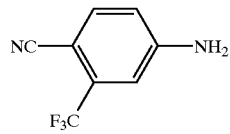

Formula VII under conditions sufficient to provide a compound having the structure of Formula VIII:

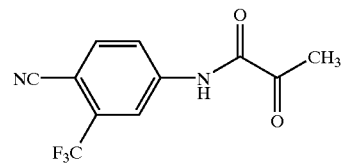

Formula VIII

The compound of Formula VIII is treated under conditions sufficient to provide bicalutamide. Preferably, the compound of Formula VIII is contacted with a compound having the structure of Formula IX:

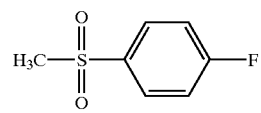

Formula IX under conditions sufficient to provide bicalutamide. Typically, the compound of Formula VIII is addition reacted with a compound having the structure of Formula IX.

As discussed in U.S. Pat. No. 5,985,868, to Gray, the (−)isomer of bicalutamide may be obtained by resolution of the enantiomers of racemic bicalutamide. Examples of standard methods of resolution known to those skilled in the art include simple crystallization and chromatographic resolution. (See, for example, G. Subramanian, *A Practical Approach to Chiral Separations by Liquid Chromatography*, John Wiley & Sons, 1994; Thomas E. Beesley, Raymond P. W. Scott, *Chiral Chromatography*, John Wiley & Son Ltd., 1999; Satinder Ahuja, *Chiral Separations: Applications and Technology*, American Chemical Society, 1996); E. L. Eliel, *Stereochemistry of Carbon Compounds*, McGraw Hill (1962); and Wilen and Lochmuller, "Tables of Resolving Agents," *J. chromatography* 113, 283–302 (1975)). In a preferred method, a racemic mixture is separated using high pressure liquid chromatography (HPLC) (see Krstulovic, A. M., ed. *Chiral Separations* by HPLC: *Applications to Pharmacological Compounds*, Halsted Press, 1989).

Optically active compounds have the ability to rotate the plane of polarized light. In describing an optically active compound, the prefixes D and L or R and S are used to denote the absolute configuration of the molecule about its chiral center(s). The prefixes "d" and "l" or (+) and (−) are used to denote the optical rotation of the compound (i.e., the direction in which a plane of polarized light is rotated by the optically active compound). The "l" or (−) prefix indicates that the compound is levorotatory (i.e., rotates the plane of polarized light to the left or counterclockwise) while the "d" or (+) prefix means that the compound is dextrarotatory (i.e., rotates the plane of polarized light to the right or clockwise). The sign of optical rotation, (−) and (+), is not related to the absolute configuration of the molecule, R and S.

Thus, in a further aspect of the invention, the R and S components of the racemic mixture prepared according to the synthetic method of the invention are separated to provide compositions having a majority of R or a majority of S enantiomer. In a preferred aspect of the invention, the R and S components of the racemic mixture prepared according to the synthetic method of the invention are separated to provide compositions comprising greater than 75 percent R or S, more preferably greater than 90 percent R or S, and still more preferably greater than 99 percent R or S. In a highly preferred embodiment, the separated compositions have substantially all R enantiomer or substantially all S enantiomer. The R form is preferred as the more active of the two enantiomers.

Acylanilides synthesized by the methods disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, lactic acid, tartaric acid, succinic acid, malic acid, ascorbic acid, benzoic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Acylanilides synthesized by the methods described above may be formulated for administration in a pharmaceutical carrier in accordance with known techniques. See, e.g., Remington, The *Science And Practice of Pharmacy* ($9^{th}$ Ed. 1995). In the manufacture of a pharmaceutical formulation according to the invention, the acylanilide (and/or the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5 percent to 95 percent or 99 percent by weight of the acylanilide. One or more acylanilides synthesized by the methods described above may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular acylanilide which is being used.

Formulations suitable for oral administration may be presented in discrete units, such as capsules, cachets, lozenges, or tables, each containing a predetermined amount of the acylanilide; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the acylanilide and a suitable carrier (which may contain one or more accessory ingredients as noted above). In general, the formulations of the invention are prepared by uniformly and intimately admixing the acylanilide with a liquid or finely divided solid carrier, or both, and then, if necessary, shaping the resulting mixture. For example, a tablet may be prepared by compressing or molding a powder or granules containing the acylanilide, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the acylanilide in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the acylanilide, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unitdose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the acylanilide with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the acylanilide. Suitable formulations comprise citrate or bistris buffer (pH6) or ethanolwater and contain from 0.1 to 0.2M active ingredient.

All starting materials used in the procedures described herein are either commercially available or can be prepared by methods known in the art using commercially available starting materials.

The present invention will now be described with reference to the following examples. It should be appreciated that these examples are for the purposes of illustrating aspects of the present invention, and do not limit the scope of the invention as defined by the claims.

EXAMPLE 1

Synthesis of N-(4-Cyano-3-trifluoromethyl-phenyl)-2-oxo-propionamide

Pyruvic acid (3.0 mL; 43 mmol) and thionyl chloride (3.1 mL; 43 mmol) were added simultaneously via syringes to a stirring solution of 4-cyano-3-trifluoromethyl-aniline (1.00 g; 5.38 mmol) in 20 mL of dry DMA at room temperature. After 10 minutes, the reaction mixture was diluted with ether and extracted 3 times with saturated NaHCO$_3$ and 4 times with cold saturated brine. The organic layer was dried with MgSO$_4$ and concentrated by rotary evaporation. The product was purified by silica gel chromatography (ethyl acetate/hexanes [1/1]). Yield 1.11 g (81%); mp 147–148° C.; MS (FAB$^+$) 257 (M+1); $^1$H NMR δ 9.12 (s, 1H), 8.15 (s, 1H), 8.01 (d, J=8.5), 7.84 (d, J=8.5, 1H), 2.59 (s, 3H); $^{13}$C NMR δ 195.66, 157.71, 140.29, 135.90, 134.2, 122.01, 121.85, 117.44, 115.12, 105.55, 23.92; $^{19}$F NMR δ –62.76. IR: 3330, 3112, 3065, 1719, 1540. UV: λ$_{max}$ 214, 248, 288. Anal. Calculated for C$_{11}$H$_7$F$_3$N$_2$O$_2$: C, 51.57; H, 2.75; N, 10.94. Found: C, 51.69; H, 2.81; N, 10.86.

EXAMPLE 2

Synthesis of N-(4-Cyano-3-trifluoromethyl-phenyl)-3-(4-fluoro-benzenesulfonyl)-2-hydroxy-2-methyl-propionamide Butyllithium (13.0 mmol) was added to a stirring solution of 4-fluorophenyl methyl sulfone (2.49 g; 14.3 mmol) in 13 mL of dry THF at room temperature. After 1 hr, a solution of the keto-amide (1.11 g; 4.34 mmol) prepared above in Example 1 in 4 mL of dry THF was added slowly to the stirring reaction. After 20 minutes, the reaction was brought to a neutral pH with 1M HCl. The contents were diluted with ethyl acetate and extracted with 1M HCl and saturated brine. The organic layer was dried with MgSO$_4$ and concentrated by rotary evaporation. After purification by silica gel chromatography (CH$_2$Cl$_2$/ethyl acetate [4/1]), the product was crystallized from ethyl acetate—petroleum ether. Yield 1.67 g (90%); mp 187° C. ; MS (FAB$^+$) 431 (M+I), 453 (M+Na); 1H NMR δ 9.08 (s, 1H), 7.98 (a, 1H), 7.87–7.92 (m, 2H), 7.79–7.78 (m, 2H), 7.15–7.20 (m, 2H), 5.04 (s, 1H), 3.97 (d, J=14.5, 1H), 3.49 (d, J=14.5, 1H), 1.62 (s, 3H); $^{19}$F NMR δ-62.74, –101.49. IR: 3432, 3338, 3106, 2921, 1699, 1586, 1525. UV: λ$_{max}$ 216, 270. Anal. Calculated for C$_{18}$H$_{14}$F$_4$N$_2$O$_4$S: C, 50.23; H, 3.28; N, 6.51. Found: C, 50.35; H, 3.16; N, 6.35.

In the specification, there has been disclosed typical preferred embodiments of the invention and, although specific terms are employed, they are used in a generic and descriptive sense only and not for purposes of limitation, the scope of the invention being set forth in the following claims.

What is claimed is:

1. A method of synthesizing an acylanilide comprising:
   contacting a compound having the structure of Formula I:

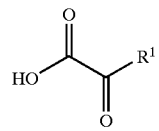

Formula I wherein
   R$^1$ is substituted or unsubstituted alkyl or haloalkyl; with a compound having the structure of Formula II:

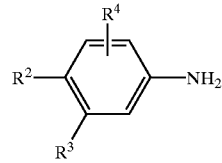

Formula II wherein
   R$^2$ is cyano, carbamoyl, nitro, fluoro, chloro, bromo, iodo, or hydrogen; or alkyl, alkoxy, alkanoyl, alkylthio, alkylsulfinyl, or alkylsulfonyl each being substituted or unsubstituted and having up to 4 carbon atoms; or phenyl, phenylthio, phenylsulfinyl or phenylsulfonyl each being susbstituted or unsubstituted;
   R$^3$ is cyano, carbamoyl, nitro, fluoro, chloro, bromo or iodo; or alkyl, alkoxy, alkanoyl, alkylthio, alkylsulfinyl, or alkylsulfonyl each being substituted or unsubstituted and having up to 4 carbon atoms; or phenyl, phenylthio, phenylsulfinyl or phenylsulfonyl each being substituted or unsubstituted; and
   R$^4$ is hydrogen or halogen; in the presence of an aprotic solvent to provide a compound having the structure of Formula III:

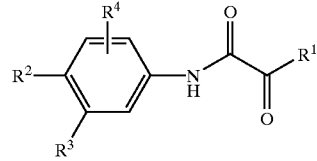

Formula III and;
   contacting a compound having the structure of Formula IV:

R$^5$—X$^1$—R$^6$—R$^7$     Formula IV wherein
   R$^5$ is substituted or unsubstituted alkyl having up to 6 carbon atoms;
   R$^6$ is a direct link, or substituted or unsubstituted alkyl having up to 6 carbon atoms;
   R$^7$ is alkyl, alkenyl, hydroxyalkyl or cycloalkyl each being substituted or unsubstituted and having up to 6 carbons; or R⁷ is phenyl which bears one, two or three substituents independently selected from hydrogen, halogen, nitro, carboxy, carbamoyl and cyano, and alkyl, alkoxy, alkanoyl, alkylthio, alkylsulfinyl, alkylsulfonyl, perfluoroalkyl, perfluoroalkoxy, perfluoroalkylthio, perfluoroalkylsulfinyl, perfluoroalkylsulfonyl, alkoxycarbonyl and N-alkylcarbamoyl each of up to 4 carbon atoms, and phenyl, phenylthio, phenylsulfinyl and phenylsulfonyl; or R⁷ is naphthyl; or R⁷ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulfinyl or alkylsulfonyl each of up to 4 carbon atoms, or oxy or hydroxy substituents, or which if sufficiently saturated may bear one or two oxo substituents; and X¹ is oxygen, sulfur, sulfinyl (—SO—), sulfonyl (—SO₂—), imino (—NH—) or alkylimino (—NR⁸—) where R⁸ is alkyl having up to 6 carbon atoms;
with an organometallic compound to provide an intermediate compound; and
contacting the intermediate compound with the compound of Formula III to provide an acylanilide having the structure of Formula V:

Formula V

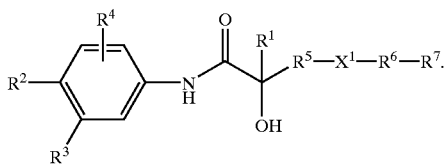

2. The method according to claim 1, wherein the contacting of the compound of Formula II with the compound of Formula I comprises contacting the compound of Formula I with the compound of Formula II in the presence of a carboxylic acid halogenating compound.

3. The method according to claim 2, wherein the carboxylic acid halogenating compound is thionyl bromide or thionyl chloride.

4. The method according to claim 2, wherein the ratio on a molar basis of carboxylic acid halogenating compound to the compound of Formula I is between about 1:2 and about 2:1.

5. The method according to claim 1, wherein the compound of Formula I reacts with the carboxylic acid halogenating compound to provide an acyl halide.

6. The method according to claim 5, wherein the acyl halide reacts with the compound of Formula II to provide the compound of Formula III.

7. The method according to claim 6, wherein the ratio on a molar basis of the compound of Formula II to acyl halide is between 1:4 and 1:12.

8. The method according to claim 6, wherein the ratio on a molar basis of the compound of Formula I to acyl halide is between 1:6 and 1:10.

9. The method according to claim 1, wherein the aprotic solvent is selected from the group consisting of N,N-dimethylacetamide, N,N-dimethylformamide, and mixtures thereof.

10. The method according to claim 1, wherein the contacting of the compound of Formula I with the compound of Formula II comprises contacting the compound of Formula I with the compound of Formula II at a temperature between about −5° C. and about 40° C.

11. The method according to claim 1, wherein the contacting of the compound of Formula I with the compound of Formula II comprises contacting the compound of Formula I with the compound of Formula II at a temperature between about 20° C. and about 30° C.

12. The method according to claim 1, wherein R¹ is substituted or unsubstituted alkyl having up to 4 carbon atoms.

13. The method according to claim 1, wherein R¹ is substituted or unsubstituted alkyl having 1 or 2 carbon atoms.

14. The method according to claim 1, wherein R¹ is methyl.

15. The method according to claim 1, wherein R² is cyano, nitro, or chloro, or perfluoroalkyl, perfluoroalkoxy, perfluoroalkylthio, perfluoroalkylsulfinyl or perfluoroalkylsulfonyl each having up to 4 carbon atoms; R³ is perfluoroalkyl, perfluoroalkoxy, perfluoroalkylthio, perfluoroalkylsulfinyl or perfluoroalkylsulfonyl each having up to 4 carbon atoms; R⁴ is hydrogen; and R⁵ is unsubstituted alkyl.

16. The method according to claim 1, wherein R¹ is methyl; R² is cyano; R³ is trifluoromethyl; and R⁴ is hydrogen.

17. The method according to claim 1, wherein the yield of the compound of Formula III is greater than about 70 percent.

18. The method according to claim 1, wherein the organometallic compound is butyllithium.

19. The method according to claim 1, wherein the contacting of the intermediate compound with the compound of Formula III comprises slowly adding the compound of Formula III to a solution containing the intermediate compound.

20. The method according to claim 1, wherein the ratio on a molar basis of the compound of Formula III to intermediate compound is between about 1:2 and about 1:10.

21. The method according to claim 1, wherein the ratio on a molar basis of the compound of Formula III to intermediate compound is between about 1:2 and about 1:5.

22. The method according to claim 1, wherein R⁵ is alkylene, R⁶ is a direct link, R⁷ is halophenyl, and X¹ is thio, sulfinyl, or sulfonyl.

23. The method according to claim 1, wherein R⁵ is methylene, R⁶ is a direct link, R⁷ is 4fluorophenyl, and X¹ is thio, sulfinyl, or sulfonyl.

24. The method according to claim 1, wherein the contacting of the compound of Formula IV with the organometallic compound occurs at a temperature between about −5° C. and about 40° C.

25. The method according to claim 1, wherein the contacting of the compound of Formula IV with the organometallic compound occurs at a temperature between about 20° C. and about 30° C.

26. The method according to claim 1, wherein an overall yield of the compound of Formula V is greater than about 50 percent.

27. The method according to claim 1, wherein an overall yield of the compound of Formula V is greater than about 60 percent.

28. The method according to claim 1, wherein an overall yield of the compound of Formula V is greater than about 70 percent.

29. A method of synthesizing bicalutamide comprising:
contacting a compound having the structure of Formula VI:

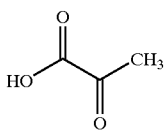

Formula VI with a compound having the structure of Formula VII;

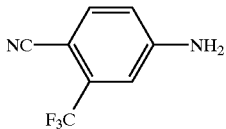

Formula VII in the presence of an aprotic solvent to provide a compound having the structure of Formula VIII:

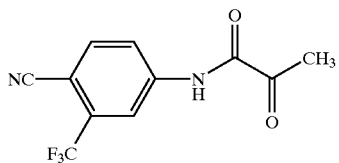

Formula VIII and;

contacting a compound having the structure of Formula IX;

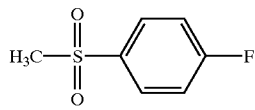

Formula IX with an organometallic compound to provide an intermediate compound; and contacting the intermediate compound with the compound of Formula VIII to provide bicalutamide.

30. The method according to claim 29, wherein the contacting of the compound of Formula VI with a compound of Formula VII comprises contacting the compound of Formula VI with the compound of Formula VII in the presence of a carboxylic acid halogenating compound.

31. The method according to claim 29, wherein the carboxylic acid halogenating compound is thionyl bromide or thionyl chloride.

32. The method according to claim 29, wherein the ratio on a molar basis of carboxylic acid halogenating compound to the compound of Formula VI is between about 1:2 and about 2:1.

33. The method according to claim 29, wherein the compound of Formula VI reacts with the carboxylic halogenating compound to provide an acyl halide.

34. The method according to claim 29, wherein the acyl halide reacts with the compound of Formula VII to provide the compound of Formula VIII.

35. The method according to claim 29, wherein the ratio on a molar basis of the compound of Formula VII to acyl halide is between about 1:4 and about 1:12.

36. The method according to claim 29, wherein the ratio on a molar basis of the compound of Formula VII to acyl halide is between about 1:6 and about 1:10.

37. The method according to claim 29, wherein the aprotic solvent is selected from the group consisting of N,N-dimethylacetamide, N,N-dimethylformamide, and mixtures thereof.

38. The method according to claim 29, wherein the contacting of the compound of Formula VI with a compound of Formula VII comprises contacting the compound of Formula VI with the compound of Formula VII at a temperature between about −5° C. and about 40° C.

39. The method according to claim 29, wherein the contacting of the compound of Formula VI with a compound of Formula VII comprises contacting the compound of Formula VI with the compound of Formula VII at a temperature between about 20° C. and about 30° C.

40. The method according to claim 29, wherein the yield of the compound of Formula VIII is greater than about 75 percent.

41. The method according to claim 29, wherein the organometallic compound is butyllithium.

42. The method according to claim 29, wherein the contacting of the compound of Formula IX with the organometallic compound occurs at a temperature between about −5° C. and about 40° C.

43. The method according to claim 29, wherein the contacting of the compound of Formula IX with the organometallic compound occurs at a temperature between about 20° C. and about 30° C.

44. The method according to claim 29, wherein an overall yield of bicalutamide is greater than about 50 percent.

45. The method according to claim 30, wherein an overall yield of bicalutamide is greater than about 60 percent.

46. The method according to claim 31, wherein an overall yield of bicalutamide is greater than about 70 percent.

* * * * *

UNITED STATES PATENT AND TRADEMARK OFFICE
CERTIFICATE OF CORRECTION

PATENT NO. : 6,479,692 B1  Page 1 of 1
DATED : November 12, 2002
INVENTOR(S) : Ekwuribe et al.

It is certified that error appears in the above-identified patent and that said Letters Patent is hereby corrected as shown below:

Column 15,
Line 50, should read as follows:
-- 5. The method according to claim 2, wherein the com- --

Column 16,
Line 46, should read as follows:
-- methylene, $R^6$ is a direct link, $R^7$ is 4-fluorophenyl, and $X^1$ --

Column 18,
Line 1, should read as follows:
-- 32. The method according to claim 31, wherein the ratio --
Line 5, should read as follows:
-- 33. The method according to claim 31, wherein the --
Line 8, should read as follows:
-- 34. The method according to claim 33, wherein the acyl --
Line 11, should read as follows:
-- 35. The method according to claim 34, wherein the ratio --
Line 14, should read as follows:
-- 36. The method according to claim 34, wherein the ratio --

Signed and Sealed this

Twenty-fourth Day of June, 2003

JAMES E. ROGAN
*Director of the United States Patent and Trademark Office*